(12) United States Patent
Youngblood et al.

(10) Patent No.: US 8,444,314 B2
(45) Date of Patent: May 21, 2013

(54) DAMPENING APPARATUS AND METHOD FOR SINGLE PISTON PUMP USED IN DETERMINING THE THERMAL STABILITY OF FLUIDS

(75) Inventors: Larry M. Youngblood, Houston, TX (US); David G. Anderson, San Antonio, TX (US); Guoxing Yang, Pearland, TX (US)

(73) Assignee: Petroleum Analyzer Company, LP, Houston, TX (US)

( * ) Notice: Subject to any disclaimer, the term of this patent is extended or adjusted under 35 U.S.C. 154(b) by 391 days.

(21) Appl. No.: 12/958,838

(22) Filed: Dec. 2, 2010

(65) Prior Publication Data

US 2012/0014409 A1 Jan. 19, 2012

Related U.S. Application Data

(63) Continuation-in-part of application No. 12/838,104, filed on Jul. 16, 2010, now Pat. No. 8,262,283.

(51) Int. Cl.
*G01N 33/22* (2006.01)
*G01N 25/00* (2006.01)

(52) U.S. Cl.
USPC .......................................... 374/43; 73/61.62

(58) Field of Classification Search
USPC ............ 374/43, 45, 57, 137; 73/61.62, 61.71, 73/61.72, 61.76
See application file for complete search history.

(56) References Cited

U.S. PATENT DOCUMENTS

| | | | |
|---|---|---|---|
| 3,670,561 A | | 6/1972 | Hundere |
| 3,782,709 A | * | 1/1974 | Gildner .......................... 267/114 |
| 3,917,531 A | * | 11/1975 | Magnussen ................... 210/101 |
| 3,984,315 A | * | 10/1976 | Ernst et al. ..................... 210/656 |
| 3,985,021 A | | 10/1976 | Achener et al. |
| 4,290,776 A | * | 9/1981 | Yamada ......................... 436/161 |
| 4,432,250 A | | 2/1984 | Albrecht et al. |
| 4,448,691 A | * | 5/1984 | Davis ............................. 210/656 |
| 4,448,692 A | * | 5/1984 | Nakamoto et al. ............ 210/656 |
| 4,919,595 A | * | 4/1990 | Likuski et al. .................. 417/18 |
| 5,101,658 A | | 4/1992 | Wilson, III et al. |
| 5,337,599 A | | 8/1994 | Hundere et al. |
| 5,468,262 A | * | 11/1995 | Acker et al. ..................... 44/348 |

(Continued)

FOREIGN PATENT DOCUMENTS

JP 61175565 A * 8/1986

OTHER PUBLICATIONS

JFTOT 230 Mark III Jet Fuel Thermal Oxidation Tester User's Manual, Alcor, PN: AL-59322, Rev. E, Aug. 14, 2008.

(Continued)

*Primary Examiner* — R. A. Smith
(74) *Attorney, Agent, or Firm* — Gunn, Lee & Cave, P.C.

(57) ABSTRACT

A thermal oxidation tester is shown for determining thermal stability of a fluid, particularly hydrocarbons when subjected to elevated temperatures. The tendency of the heated fluid to oxidize and (1) form deposits on a surface of a heater tube and (2) form solids therein, are both measured at a given flow rate, temperature and time. The measured results are used to determine whether a fluid sample passes or fails the test. Results of the measurements are recorded. The fluid under test is pumped with a low volume, high pressure, single piston pump with only a small fluctuation (pulsation) in output flow.

12 Claims, 14 Drawing Sheets

U.S. PATENT DOCUMENTS

| | | |
|---|---|---|
| 7,093,481 B2 | 8/2006 | Morris |
| 8,215,922 B2 * | 7/2012 | Berger et al. ............. 417/205 |
| 2002/0083760 A1 * | 7/2002 | Morris ..................... 73/61.76 |

OTHER PUBLICATIONS

Maxim, DS2433X Flip Chip Pkg, 1.10 MM Pitch Pkg Code BF623-3, Walker, Jeff, Jul. 16, 2008, Rev. A, effective date Jul. 16, 2008.

JFTOT® 230 Mark III, "Smaller, Simpler, Faster. Improved Controls for Jet Fuel Stability Analysis." PAC, 2 pages.

JFTOT, "Video Tube Deposit Rater", PAC, 2 pages.

ASTM D 3241-09, "Standard Test Method for Thermal Oxidation Stability of Aviation Turbine Fuels (JFTOT Procedure)", ASTM International, 14 pages.

* cited by examiner

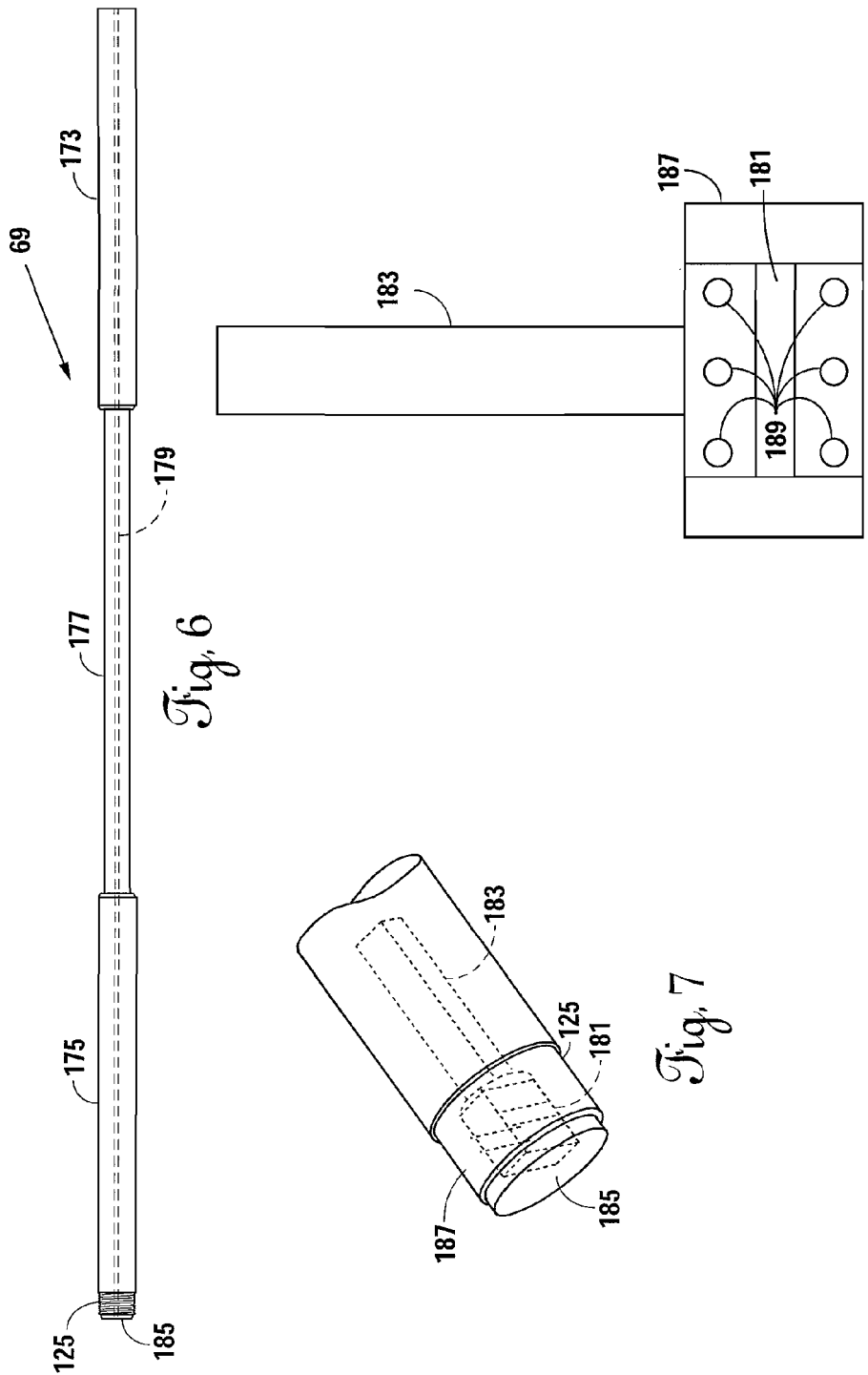

DAMPENING APPARATUS AND METHOD FOR SINGLE PISTON PUMP USED IN DETERMINING THE THERMAL STABILITY OF FLUIDS

CROSS REFERENCE TO RELATED APPLICATIONS

This is a continuation-in-part of U.S. patent application Ser. No. 12/838,104, filed Jul. 16, 2010.

BACKGROUND OF THE INVENTION

1. Technical Field

This invention relates to methods and devices for measuring the thermal characteristics of fluids. Specifically, this invention relates to the dampening apparatus and method for a single piston pump used in a system to measure the thermal oxidation tendencies of fuels for liquid hydrocarbon-burning engines.

2. Background Art

When engines were developed for use in jet aircraft, problems began to develop for jet fuel due to poor fuel thermal stability. At higher temperatures, the jet fuels would oxidize and form deposits that would clog fuel nozzles and fuel filters. These deposits would also collect in the jet engine.

While various tests were devised and used in the 1950s and 60s to rate the thermal oxidation characteristics of jet fuels prior to being used in jet aircraft, Alf Hundere developed the apparatus and method which became the standard in the industry. In 1970, Alf Hundere filed what became U.S. Pat. No. 3,670,561, titled "Apparatus for Determining the Thermal Stability of Fluids". This patent was adopted in 1973 as ASTM D3241 Standard, entitled "Standard Test Method for Thermal Oxidation Stability of Aviation Turbine Fuels", also known as the "JFTOT® Procedure". This early Hundere patent was designed to test the deposition characteristics of jet fuels by determining (1) deposits on the surface of a heater tube at an elevated temperature and (2) differential pressure across a filter due to collection of particulate matter. To this day, according to ASTM D3241, the two critical measurements are still (1) the deposits collected on a heater tube and (2) differential pressure across the filter due to the collection of particulate matter on the filter.

According to ASTM D3241, 450 mL of fuel flows across an aluminum heater tube at a specified rate, during a 2.5 hour test period at an elevated temperature. Currently six different models of JFTOT®[1] instruments are approved for use in the ASTM D3241-09 Standard. The "09" refers to the current revision of the ASTM D3241 Standard.

[1] JFTOT is the registered trademark of Petroleum Analyzer Company, LP.

While over the years various improvements have been made in the apparatus to run the tests, the basic test remains the same. Improvements in the apparatus can be seen in U.S. Pat. Nos. 5,337,599 and 5,101,658. The current model being sold is the JFTOT 230 Mark III, which is described in further detail in the "Jet Fuel Thermal Oxidation Tester—User's Manual". The determination of the deposits that occur on the heater tube can be made visually by comparing to known color standards or can be made using a "Video Tube Deposit Rater" sold under the Alcor mark.

The determination of the amount of deposits formed on the heater tube at an elevated temperature is an important part of the test. The current ASTM D3241 test method requires a visual comparison between the heater tube deposits and known color standard. However, this involves a subjective evaluation with the human eye. To take away the subjectivity of a person, an electronic video tube deposit rater was developed.

Also, there has been considerable discussion as to the polish or finish of the heater tube. (See U.S. Pat. No. 7,093,481 and U.S. Patent Application Publication No. US 2002/083,760.) The finish of the heater tube is very important in determining the amount of fuel deposits that will form thereon. Therefore, it is important that the quality of the finish on heater tubes made today be consistent with the finish of heater tubes made since 1973.

Once the thermal oxidation stability test has been performed on a batch of fuel, the recorded information and the heater tube are preserved to show the batch of fuel was properly tested. The information that was recorded when testing a batch of fuel is maintained separately from the heater tube itself. This can cause a problem if one or the other gets misplaced or lost. Inaccurate information and/or conclusions occur if the wrong set of data is associated with the wrong heater tube.

In prior versions of the JFTOT, a low volume, high pressure pump has been used that has two pistons. A less expensive single piston pump caused too large of a variation in output pressure to be used, especially when pumping at such a low volume and high pressure.

BRIEF SUMMARY OF THE INVENTION

It is an object of the present invention to provide an apparatus and method for testing thermal oxidation stability of fluids, particularly aviation fuels.

It is another object of the present invention to provide an apparatus and method to measure the tendency of fuels to form deposits when in contact with heated surfaces.

It is another objective of the present invention to provide an apparatus and method for testing the thermal oxidation tendency of fuels utilizing a test sample to determine if solid particles will form in the fuel at an elevated temperature and pressure.

It is another objective of the present invention to provide an apparatus and method for determining thermal oxidation stability of a batch of aviation fuel by testing a sample at an elevated temperature and pressure to determine (1) deposits that form on a metal surface and (2) solid particles that form in the fuel.

It is another objective of the present invention to provide an apparatus and method for recording and storing the thermal oxidation tendency data of fuels in single location.

It is yet another objective of the present invention to provide an intelligent heater tube on which a thermal oxidation stability test is performed with deposits collecting thereon and a memory device on one end of the intelligent heater tube to record all of the test information.

It is another objective of the present invention to have an intelligent heater tube with a memory device on one end thereon on which all of the test information in association with that heater tube can be recorded.

It is another object of the present invention to provide a memory device for an intelligent heater tube that has a ground and data connection with the memory device being connected to the heater tube.

It is another object of the present invention to provide an apparatus and method for testing thermal oxidation tendencies of high performance fuels with the test results being written into a memory device on an intelligent heater tube.

It is still another object of the present invention to provide dampening for a low volume, high pressure, single piston pump so that such a pump can be used when testing thermal oxidation stability of fluids, particularly aviation fuels.

BRIEF DESCRIPTION OF THE DRAWINGS

FIG. 6 is a lengthwise view of an intelligent heater tube.

FIG. 7 is an exploded perspective end view of the intelligent heater tube of FIG. 6, showing the EEPROM in broken lines inside of a memory device on the intelligent heater tube.

FIG. 8 is an elevated view of the 1-Wire EEPROM used in the memory device of FIG. 7.

DESCRIPTION OF THE PREFERRED EMBODIMENT

Figure 1:
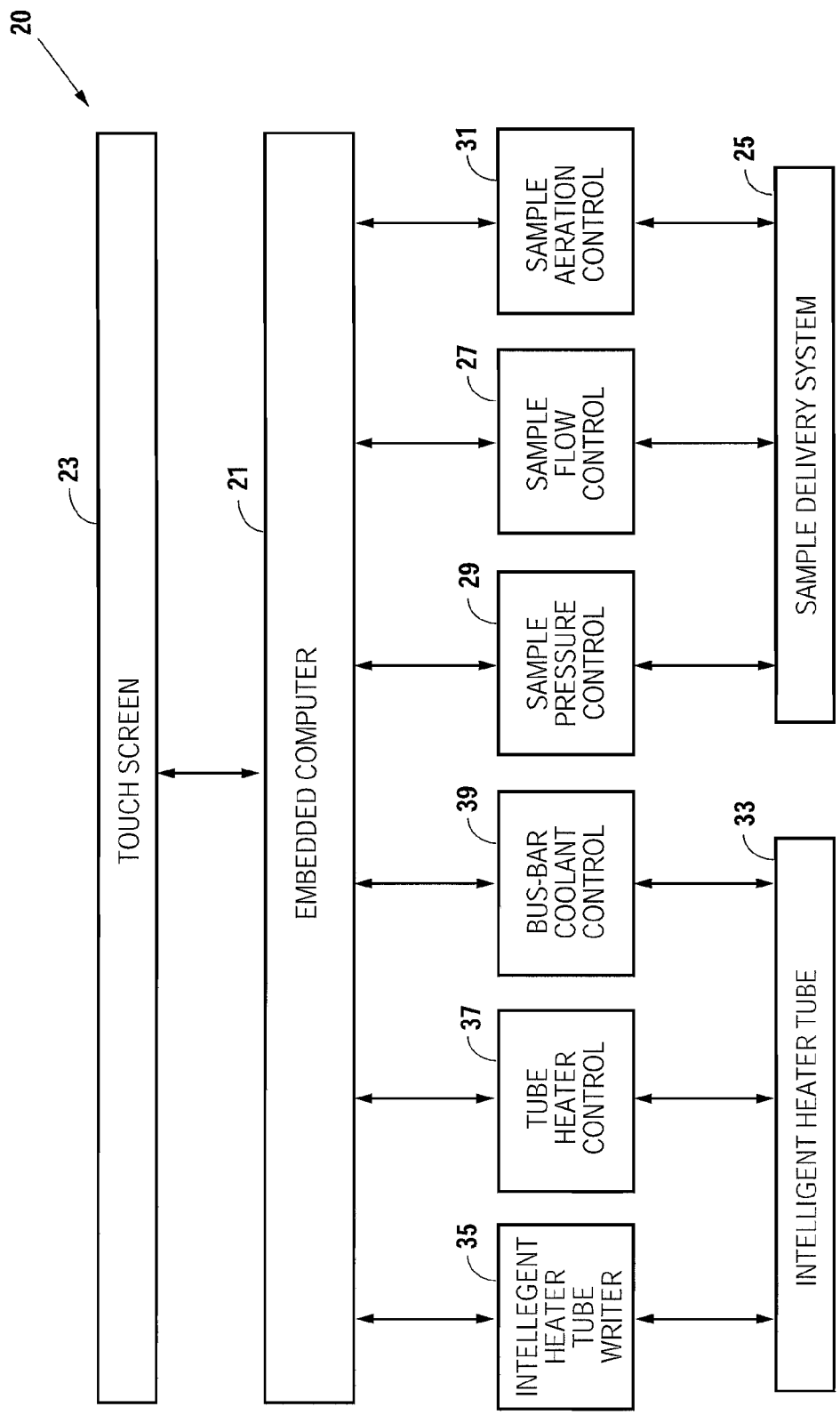
FIG. 1 is a general block diagram of a thermal oxidation stability test apparatus illustrating flow and electrical controls.

FIG. 1 is a schematic block diagram of a thermal oxidation stability tester referred to generally by the reference numeral 20. The thermal oxidation stability tester 20 has an embedded computer 21 with a touch screen 23 for user interface. While many different types of programs could be run, in the preferred embodiment, Applicant is running C++ in the embedded computer 21. The touch screen 23 displays all of the information from the thermal oxidation stability tester 20 that needs to be conveyed to the user. The user communicates back and forth with the embedded computer 21 through the touch screen 23. If a batch of fuel is to be tested, a test sample is put in the sample delivery system 25.

It is important to the test to make sure the test sample is oxygen saturated through aeration. Therefore, the embedded computer 21 operates a sample aeration control 31 for a period of time to make sure the sample is fully aerated. The aeration of the sample takes place at the beginning of the test.

The embedded computer 21 turns on a sample flow control 27, which is a pump used to deliver the sample throughout the thermal oxidation stability tester 20. Simultaneous with the sample flow control 27 pumping the test sample throughout the system, sample pressure control 29 maintains a fixed pressure throughout the system. It is important to maintain pressure in the system to prevent boiling of the test sample when at elevated temperatures. In the present thermal oxidation stability tester 20, the sample is maintained at approximately 500 psi when undergoing the thermal oxidation stability test.

Also, the embedded computer 21 controls parameters affecting the intelligent heater tube 33. The test data is recorded to the intelligent heater tube 33 via intelligent heater tube writer 35 from the embedded computer 21. Critical test parameters are recorded on a memory device (as described subsequently) on an end of the intelligent heater tube 33 via the intelligent heater tube writer 35. The rating of the deposit formed on the intelligent heater tube 33 will be recorded on the memory device at a later time.

In performing the thermal oxidation stability test on a test sample, the intelligent heater tube 33 is heated by tube heater control 37. The tube heater control 37 causes current to flow through the intelligent heater tube 33, which causes it to heat up to the temperature set point.

To prevent the hot intelligent heater tube 33 from heating other parts of the thermal oxidation stability tester 20, bus-bar coolant control 39 provides coolant upper and lower bus-bars holding each end of the intelligent heater tube 33. This results in the center section of the intelligent heater tube 33 reaching the prescribed temperature while the ends of the intelligent heater tube 33 are maintained at a lower temperature. This is accomplished by flowing coolant via the bus-bar coolant control 39 across the ends of the intelligent heater tube 33.

The test parameters, such as the dimension of the heater tube, pressure of the test sample or flow rate are fixed by ASTM D3241 However, the control of these parameters are the focus of this invention.

Figure 2:
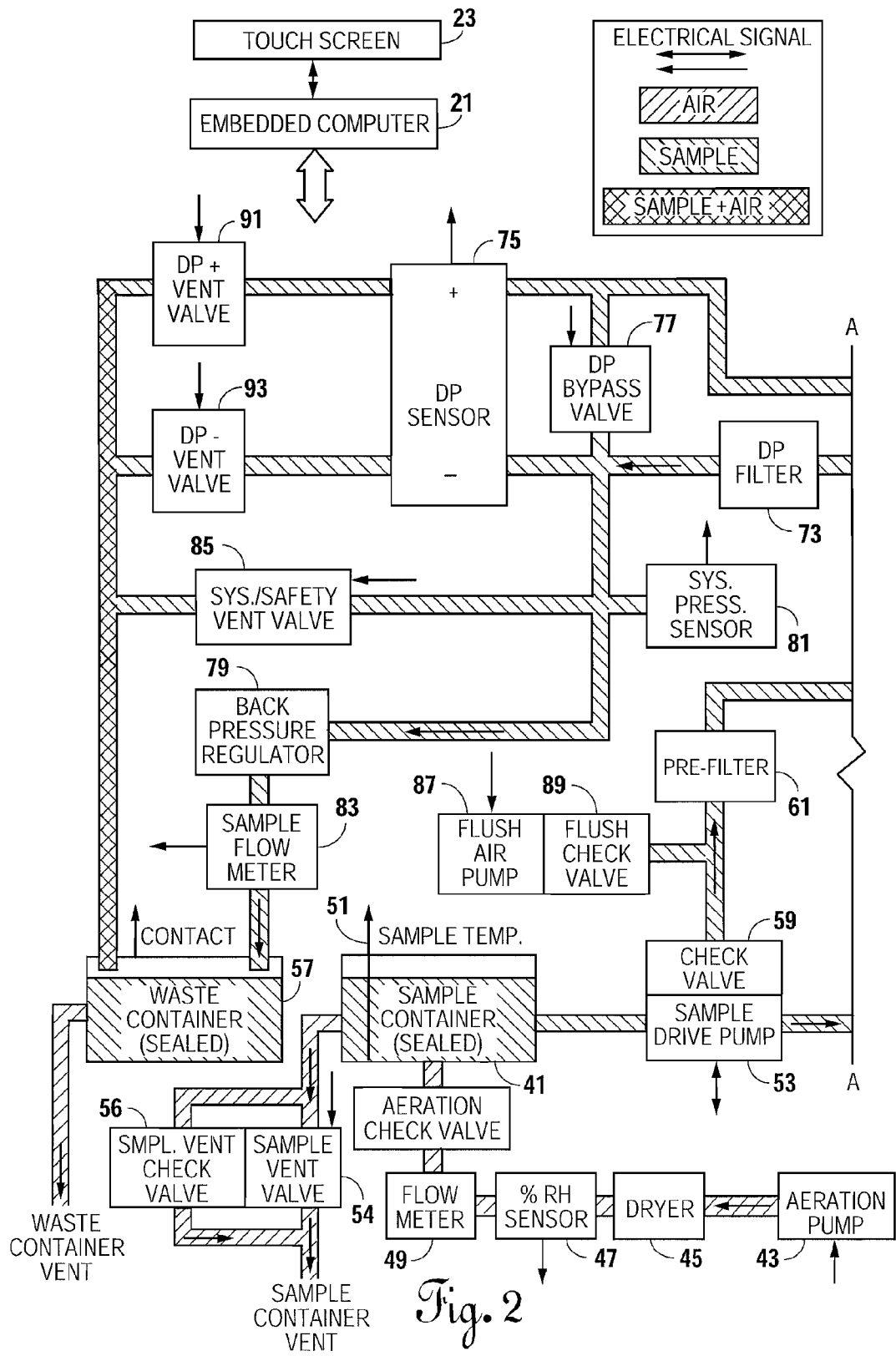
FIGS. 2 and 2A are a more detailed block diagram showing a thermal oxidation test apparatus used to perform ASTM D3241 Standard.
Figure 2A:
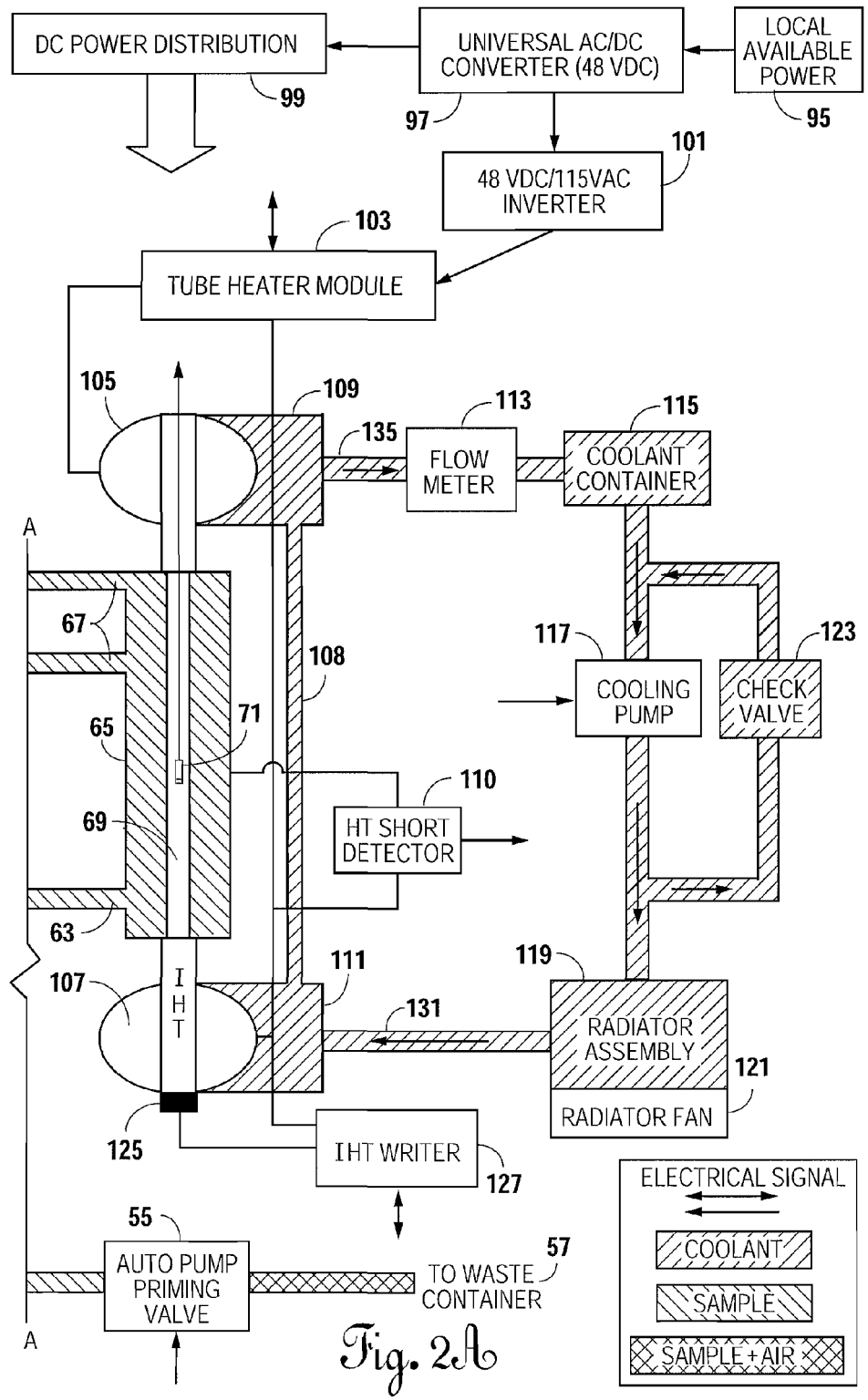

Referring now to FIGS. 2 and 2A in combination, a schematic flow diagram is shown connecting the mechanical and electrical functions. The embedded computer 21 and the touch screen 23 provide electrical signals as indicated by the arrows. A test sample is contained in the sample container 41. To make sure the sample and the sample container 41 is fully aerated, an aeration pump 43 is turned ON. The aeration pump 43 pumps air through a dryer 45 where the air is dehumidified to remove moisture. From the dryer 45, a percent relative humidify sensor 47 determines the humidity level of the pumped air and provides that information to the embedded computer 21. Assuming the percent humidity of the pumped air is sufficiently low, the test procedure will continue pumping air through the flow meter 49 and aeration check valve 50 into the sample container 41. During aeration, flow meter 49 should record approximately 1.5 liters of air per minute. Since the flow meter 49 runs for approximately six minutes, the aeration pump 43 will sparge approximately nine liters of air into the test sample. This is sufficient time to saturate the test sample with dry air.

Within the sample container 41, a sample temperature measurement 51 is taken and provided to the embedded computer 21. The sample temperature measurement 51 is to ensure that the test sample is between 15°-32° C. If the test sample is outside of this temperature range, results can be impacted. Therefore, if the test sample is outside this temperature range, the embedded computer 21 would not let the test start.

Once the test sample has been aerated and if all the other parameters are within tolerance, then the sample drive pump 53 will turn ON. The sample drive pump 53 is a single piston HPLC pump, also known as a metering pump. With every stroke of the piston, a fixed volume of the sample is delivered. The speed of the sample drive pump 53 is controlled so that it pumps 3 mL/min of the test sample. The sample drive pump 53 is configured for fast refill which minimizes the need for manual pump priming. Pulsations, associated with pumps of this design are minimized with the use of a pulse dampener and a coil tubing on the outlet side as will be subsequently described.

To get air out of the tubing between the sample container 41 and the sample drive pump 53 at the start of the test, an auto pump priming valve 55 is opened, a sample vent valve 54 is closed and the aeration pump 43 is turned ON by the embedded computer 21. The auto pump priming valve 55 opens and remains open while a combination of sample and air is discharged into waste container 57. At the same time the aeration pump 43 provides positive pressure in the sample container 41 to force test sample from the sample container 41 to the sample drive pump 53. The sample vent valve 54 closes to prevent venting of the air pressure to atmosphere to maintain a pressure of 2 to 3 psi. A sample vent check valve 56 across the sample vent valve 54 opens at 5 psi to prevent the pressure in the sample container 41 from exceeding 5 psi. Once the sample drive pump 53 starts pumping the test sample, auto pump priming valve 55 will close and the sample vent valve 54 will open. Thereafter, the sample drive pump 53 will pump the test sample through check valve 59 to the prefilter 61. The check valve 59 prevents fluid from flowing backwards through the sample drive pump 53. The check valve 59 operates at a pressure of approximately 5 psi. The check valve 59 prevents siphoning when the sample drive pump 53 is not pumping. Also, check valve 59 prevents fluid from being pushed backwards into the sample drive pump 53.

The pre-filter 61 removes solid particles in the test sample that could affect the test. The pre-filter 61 is a very fine filter, normally in the order of 0.45 micron in size. The purpose of the pre-filter 61 is to make sure particles do not get into the test filter as will be described. The pre-filter 61 is replaced before every test.

From the pre-filter 61, the test sample flows through an inlet 63 into the cylindrical heater tube test section 65. Outlet 67, while illustrated as two separate outlets, is actually a single outlet at the upper end of the cylindrical heater tube test section 65. Extending through the cylindrical heater tube test section 65 is the intelligent heater tube 69, sealed at each end with ceramic bushings and an o-ring (not shown). While the test sample flows through the cylindrical heater tube test section 65 via inlet 63 and outlet 67 and around the intelligent heater tube 69, the housing of the cylindrical heater tube test section 65 is electrically isolated from the intelligent heater tube 69. Only the test sample comes in contact with the center section of the intelligent heater tuber 69. Inside of the intelligent heater tube 69 is a thermocouple 71 that sends a signal back to the embedded computer 21 as to the temperature of the center section of the intelligent heater tube 69.

Test sample flowing from the cylindrical heater tube test section 65 flows through a differential pressure filter 73, commonly called the "test filter". In a manner as will be explained in more detail, the intelligent heater tube 69 heats up the test sample inside of the cylindrical heater tube test section 65 to the test parameter set point. Heating of the test sample may result in degradation of the test sample, or cause solid particles to form. The solid particles may deposit on the center section of the intelligent heater tube 69, and/or may collect on the differential pressure filter 73. The pressure drop across the differential pressure filter 73 is measured by differential pressure sensor 75. Pressure across the differential pressure filter 73 is continuously monitored by the embedded computer 21 through the differential pressure sensor 75. When the pressure across the differential pressure filter 73 exceeds a predefined differential of approximately 250 mm to 280 mm of mercury, the differential pressure bypass valve 77 opens to relieve the pressure. By test definition, exceeding a differential pressure of 25 mm Hg results in failure of the test.

For this test to be performed, the test sample must remain as a liquid. At typical testing temperatures of 250° C. to 350° C., many hydrocarbon fuels will transition to the vapor phase at ambient pressures. To keep the test sample in the liquid phase, the back pressure regulator 79 maintains approximately 500 psi pressure in the system. This system pressure is monitored by the system pressure sensor 81, which reports information to the embedded computer 21. During a test, normal flow of a test sample is through differential pressure filter 73 and through the back pressure regulator 79. From the back pressure regulator 79, the test sample flows through sample flow meter 83 to waste container 57. The sample flow meter 83 accurately measures the flow rate of the test sample during the test. The sample flow meter 83 provides sample flow rate information to the embedded computer 21.

A system/safety vent valve 85 is connected into the system and controlled via the embedded computer 21. The system/safety vent valve 85 acts to relieve excess system pressure in the case of power loss, improperly functioning system components or other system failures. In the event of this occurrence, the system pressure sensor 81 sends a signal to the embedded computer 21, triggering the system/safety vent valve 85 to open and relieve excess pressure. Also, at the completion of a test, the system/safety vent valve 85 opens to vent pressure from the system. The system/safety vent valve 85 is normally set to the open position requiring a program command to through the embedded computer 21 to close the system/safety vent valve 85. Therefore, if power is lost, the system/safety vent valve 85 automatically opens.

At the end of the test, after the system/safety vent valve 85 is opened and system pressure is relieved, the flush air pump 87 turns ON and flushes air through flush check valve 89 to remove the test sample from the system. The flush air pump 87 pushes most of the test sample out of the system via the system/safety vent valve 85 into the waste container 57.

The system may not operate properly if there are air pockets or air bubbles in the system. During a test, it is important to maintain an air-free system. Therefore, at the beginning of each test, the solenoid operated differential pressure plus vent valve 91 and the differential pressure minus vent valve 93 are opened so that the test section 65, differential pressure filter 73, differential pressure sensor 75 and connecting differential pressure line are, flushed with test sample, and vented to remove any air pockets that may be present. During the beginning of each test, the position of the differential pressure vent valves 91 and 93 ensure there is no air in the differential pressure lines.

If the waste container 57 is properly installed in position, a signal will be fed back to the embedded computer 21 indicating the waste container 57 is correctly connected. This also applies for the sample container 41 which sends a signal to the embedded computer 21 when it is properly connected. The system will not operate unless both the waste container 57 and the sample container 41 are properly positioned.

The center portion of the intelligent heater tube 69 is heated to the test parameter set point by flowing current through the intelligent heater tube 69. Instrument power supplied for current generation and all other instrument controls is provided through local available power 95. Depending on local power availability, local available power 95 may vary drastically. In some areas it is 50 cycles/sec. and in other areas it is 60 cycles/sec. The voltage range may vary from a high of 240 Volts down to 80 Volts or less. A universal AC/DC converter 97 takes the local available power 95 and converts it to 48 Volts DC. With the universal AC/DC converter 97, a good, reliable, constant 48 Volts DC is generated. The 48 Volts DC from the universal AC/DC converter 97 is distributed throughout the system to components that need power through the DC power distribution 99. If some of the components need a voltage level other than 48 Volts DC, the DC power distribution 99 will change the 48 Volts DC to the required voltage level.

To heat the intelligent heater tube 69, the 48 Volts from the universal AC/DC converter 97 is converted to 115 Volts AC through 48 Volt DC/115 Volts AC inverter 101. While taking any local available power 95, running it through a universal AC/DC converter 97 and then changing the power back to 115 Volts AC through DC/AC inverter 101, a stable power supply is created. While this design uses 48 Volts DC, it is possible to use a universal AC/DC converter and DC/AC inverter that operates with other voltages such as 12 Volts DC, 24 Volts DC or 230 Volts AC. From the 48 Volts DC/115 Volts AC inverter 101, power is supplied to the heater tube module 103. The heater tube module 103 then supplies current that flows through the intelligent heater tube 69 via upper clamp 105 and lower clamp 107. The heater tube module 103 is controlled by the embedded computer 21 so that during a normal test, the thermocouple 71 inside of the intelligent heater tube 69 will indicate when the intelligent heater tube 69 has reached the desired temperature.

While the center section of the intelligent heater tube 69 heats to desired test set point, the ends of the intelligent heater tube 69 should be maintained near room temperature. To maintain the ends of the intelligent heater tube 69 near room temperature, a coolant flows through an upper bus-bar 109 and lower bus-bar 111. The coolant inside the upper bus-bar 109 and lower bus-bar 111 cools the upper clamp 105 and lower clamp 107 which are attached to the ends of the intelligent heater tube 69. The preferred cooling solution is a mixture of approximately 50% water and 50% antifreeze (ethylene glycol). As the coolant flows through electrically non-conductive conduit 135 to the coolant container 115, the flow is measured by flow meter 113. To circulate the coolant, a cooling pump 117 pumps the coolant solution into a radiator assembly 119. Inside of the radiator assembly 119, the coolant is maintained at room temperature. The radiator fan 121 helps remove heat from the coolant by drawing air through the radiator assembly 119. From the radiator assembly 119, the coolant flows through electrically non-conductive conduit 131 into the lower bus-bar 111 then through electrically non-conductive conduit 108 to upper bus-bar 109 prior to returning via the flow meter 113.

The flow meter 113 is adjustable so that it can ensure a flow of approximately 10 gal./hr. The check valve 123 helps ensure the cooling system will not be over pressurized. Check valve 123 will open at around 7 psi, but normally 3-4 psi will be developed when running the coolant through the entire system.

To determine if the intelligent heater tube 69 is shorted to the test section housing (65 in FIG. 2), a heater tube short detector 110 monitors a short condition. If a short is detected, the embedded computer 21 is notified and the test is stopped.

On one end of the intelligent heater tube 69 there is a memory device 125 to which information concerning the test can be recorded by IHT writer 127 as will be discussed in more detail. While a test is being run on a test sample, the IHT writer 127 will record information into the memory device 125. At the end of the test, all electronic information will be recorded onto the memory device 125 of the intelligent heater tube 69, except for the manual tube deposit rating. To record this information, the intelligent heater tube 69 will have to be moved to another location to record the deposit rating either (a) visually or (b) through a Video Tube Deposit Rater. At that time, a second IHT writer will write onto the memory device 125. The Video Tube Deposit Rater may be built into the system or may be a standalone unit.

The intelligent heater tube 69 is approximately 6¾" long. The ends are approximately 3⁄16" in diameter, but the center portion that is heated is approximately ⅛" in diameter. Due to very low electrical resistance of aluminum, approximately 200 to 250 amps of current flows through the intelligent heater tube 69. Both the voltage and the current through the intelligent heater tube 69 is monitored by the embedded computer 21, but also the temperature of the center section of the intelligent heater tube 69 is monitored by the thermocouple 71 which is also connected to the embedded computer 21. The objective is to have the center section of the intelligent heater tube 69 at the required temperature. To generate that type of stable temperature, a stable source of power is provided through the universal AC/DC converter 97 and then the 48 VDC/115 VAC inverter 101. By using such a stable source of power, the temperature on the center section of the heater tube 69 can be controlled within a couple of degrees of the required temperature even if the local available power is unstable.

Figure 3:
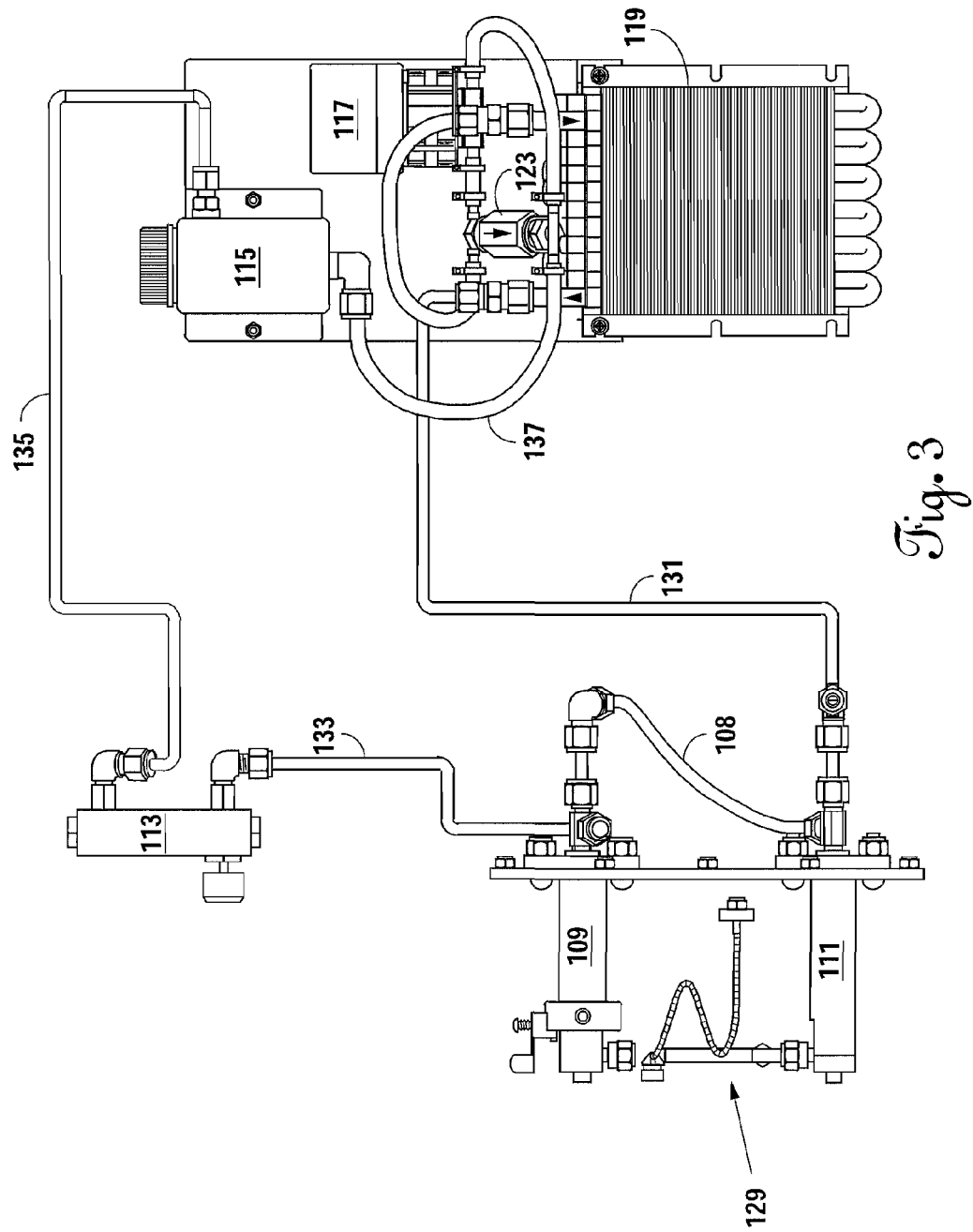
FIG. 3 is a pictorial diagram of the coolant flow for FIGS. 2 and 2A.

Referring now to FIG. 3 of the drawings, a pictorial representation of the coolant flow during a test is illustrated. Like numbers will be used to designate similar components as previously described. A pictorial illustration of the heater tube test section 129 is illustrated on the lower left portion of FIG. 3. Coolant from the radiator assembly 119 is provided to the lower bus-bar 111 via conduit 131 then to upper bus-bar 109 via conduit 108. From the upper bus-bar 109, the coolant flows via conduit 133 to flow meter 113. From flow meter 113, the coolant flows through conduit 135 to the coolant container 115. The cooling pump 117 receives the coolant through conduit 137 from the coolant container 115 and pumps the coolant into radiator assembly 119. If the pressure from the cooling pump 117 is too high, check valve 123 will allow some of the coolant to recirculate around the cooling pump 117. FIG. 3 is intended to be a pictorial representation illustrating how the coolant flows during a test.

Figure 4:
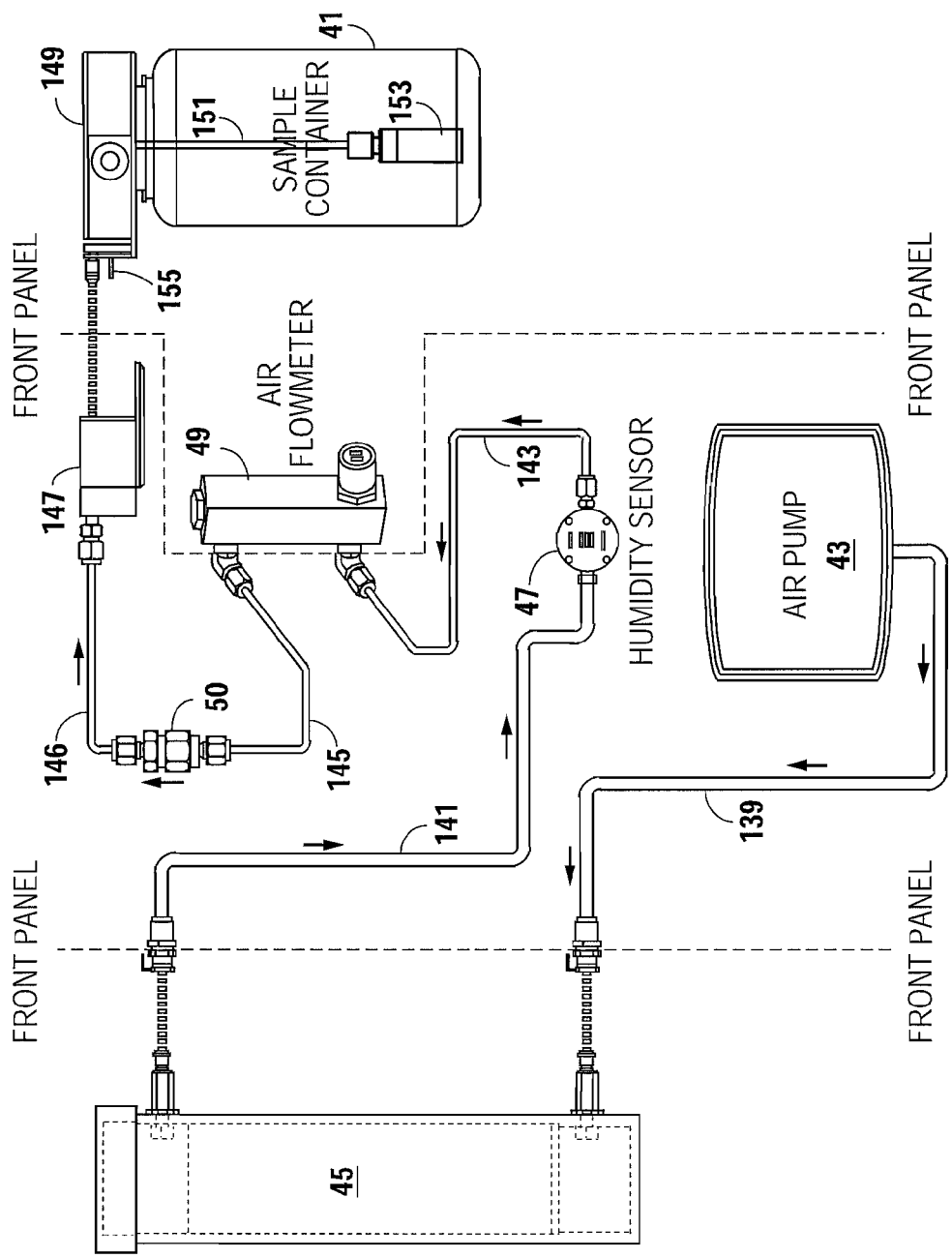
FIG. 4 is a pictorial diagram of the airflow in FIGS. 2 and 2A

Likewise, FIG. 4 is a pictorial representation of the aeration system for the test sample. Similar numbers will be used to designate like components as previously described. An aeration pump 43 pumps air through conduit 139 to a dryer 45. The dryer 45 removes moisture from the air to prevent the moisture from contaminating the test sample during aeration. From the dryer 45, the dried air will flow through conduit 141 to humidity sensor 47. If the percent relative humidity of the dried air blowing through conduit 141 exceeds a predetermined amount of 20% relative humidity, the system will shut down. While different types of dryers 45 can be used, it was found that Dry-Rite silica gel desiccant is an effective material for producing the desired relative humidity.

From the percent humidity sensor 47, the dried air flows through conduit 143 to flow meter 49, which measures the air flow through conduit 143 and air supply conduit 145. From air supply conduit 145, the dried air flows through aeration check valve 50 and conduit 146 sample container arm mounting clamp 147 and sample container arm 149 to aeration conduit 151 located inside of sample container 41. In the bottom of sample container 141, a glass frit 153 connects to aeration conduit 151 to cause the dried air to sparge through the test sample in sample container 41. When the sample container 41 is in place and the sample container arm 149 is connected to the sample container arm mounted clamp 47, contact 155 sends a signal to the embedded computer 21 (see FIG. 2) indicating the sample container 41 is properly installed.

Figure 5:
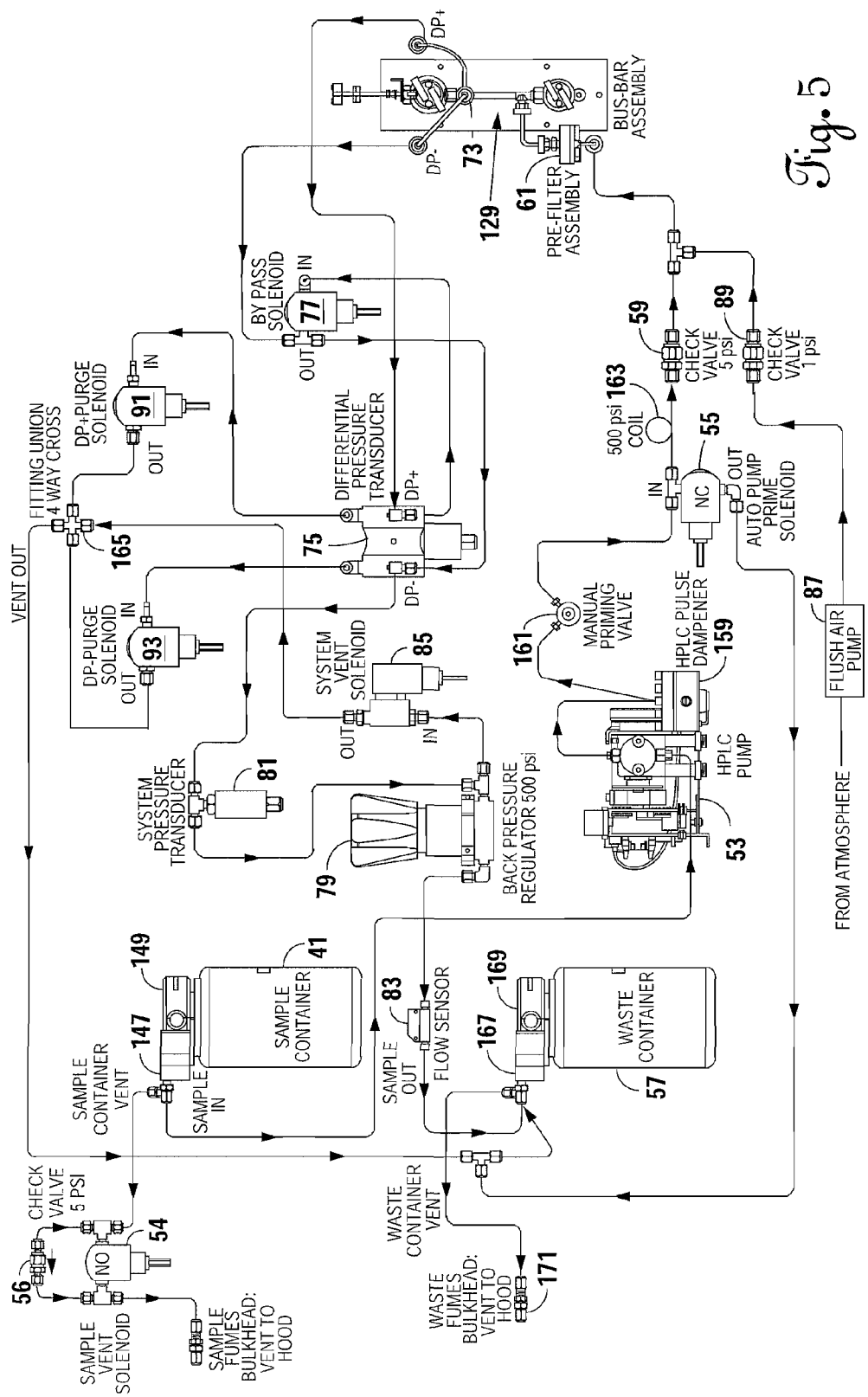
FIG. 5 is a pictorial diagram showing flow of the test sample in FIGS. 2 and 2A.

Referring now to FIG. 5, a pictorial illustration of the flow of the test sample in connection with FIGS. 2 and 2A is shown in a schematic flow diagram. The test sample is contained in sample container 41, which is connected via sample container arm 149 to the sample container arm mounting clamp 147. Vapors given off by the test sample are discharged through a vent 157, normally through a vent hood to atmosphere. Simultaneously, the sample drive pump 53 draws some of the test sample out of the sample container 41. The sample drive pump 53 is a single stroke HPLC pump connected to a pulse dampener. While the pulse dampener 159 may be configured a number of ways, the pulse dampener 159 in the preferred configuration has a diaphragm with a semi-compressible fluid on one side of the diaphragm. This fluid is more compressible than the test sample thereby reducing pressure changes on the test sample flow discharged from the sample drive pump 53. The sample drive pump 53 is connected to auto pump priming valve 55. During start-up, the closed auto pump priming valve 55 opens until all of the air contained in the pump and the lines are discharged into the waste container 57. In case it is needed, a manual priming valve 161 is also provided. Additionally, the aeration pump 43 is turned ON to provide a slight pressure in the sample container 41 of about 2 to 3 psi. The sample vent valve 54 closes to prevent this pressure escaping to atmosphere. This pressure will help push the fluid sample from the sample container 41 to the inlet of the sample drive pump 53. The 5 psi check valve 56 prevents the pressure in the sample container exceeding 5 psi. During the test, coil 163 also provides further dampening in addition to the pulse dampener 159. Check valve 59 ensures there is no back flow of the sample fuel to the sample drive pump 53. However, at the end of a test, flush check valve 89 receives air from flush air pump 87 to flush the test sample out of the system.

During normal operation of a test, the sample fuel will flow through check valve 59 and through a pre-filter 61 removing most solid particles. Following the pre-filter 61, the test sample flows into the heater tube test section 129 and then through the differential pressure filter 73. Each side of the differential pressure filter 73 connects to the differential pressure sensor 75. Also connected to the differential pressure filter 73 is the back pressure regulator 79. The pressure on the system is continuously monitored through the system pressure transducer 81. If for any reason pressure on the system needs to be released, system/safety vent valve 85 is de-energized and the pressurized test sample is vented through the four-way cross connection 165 to the waste container 57.

At the beginning of the test, to ensure there is no air contained in the system, the differential pressure plus vent valve 91 and the differential pressure minus vent valve 93 are opened to vent any pressurized fluid through the four-way cross connection 165 to the waste container 57.

In case the differential pressure filter 73 clogs so that the differential pressure exceeds a predetermined value, differential pressure bypass valve 77 will open to relieve the pressure.

To determine the exact flow rate of the test sample through the system, the sample flow meter 83 measures the flow rate of test sample from the back pressure regulator 79 before being discharged through the waste container arm 167 and the waste container clamp 169 into the waste container 57. The waste container 57 is vented all the time through vent 171.

Intelligent Heater Tube (IHT)

The intelligent heater tube (IHT) 69 is shown in FIG. 6. The intelligent heater tube 69 is cylindrical in shape as described previously. The top 173 and bottom 175 are 3/16" in diameter. The test section 177 is 1/8" in diameter. Extending longitudinally along the center axis of the intelligent heater tube 69 is a center bore 179. The thermocouple 71 (previously described in conjunction with FIG. 2A) is located inside the center bore 179. At the end of the enlarged bottom 175 is a memory device 125. The memory device 125 is slightly smaller in diameter than the heater tube bottom 175.

As shown in FIGS. 7 and 8 in combination with FIG. 6, an EEPROM 181 is located inside of the memory device 125. The EEPROM 181 only has a data signal and a ground signal. The ground signal connects to ground stick 183 and the data signal connects to data plate 185. The ground stick 183 fits inside of the center bore 179 of the intelligent heater tube 69. The EEPROM 181 is contained inside of insulated housing 187 of the memory device 125. The data plate 185 is on the end of the insulated housing 187 and is slightly smaller in diameter than the insulated housing 187. The only two connections to the memory device 125 are through the ground stick 183 and the data plate 185.

While the EEPROM 181 has a total of six solder connections 189, only two of them are connected to either the ground stick 183 or data plate 185. The data plate 185 is made from a material that will not tarnish easily such as phosphorous bronze or beryllium copper. The entire memory device 125 is resistant to degradation from jet fuel or related materials. To ensure there is no accidental electrical connection, the data plate 185 is slightly smaller in diameter than the insulated housing 187 of memory device 125, which in turn is slightly smaller in diameter than the enlarged bottom 175 of the intelligent heater tube 69.

Figure 9:
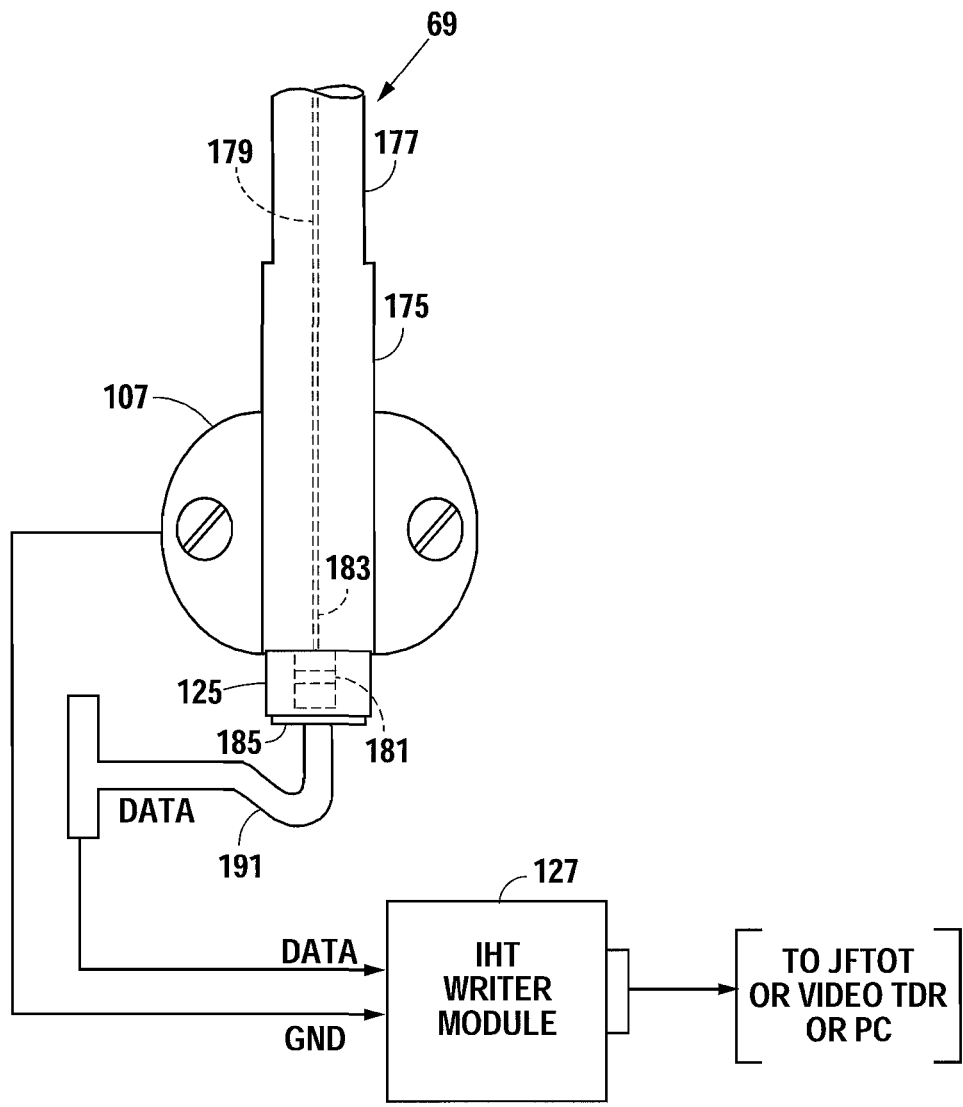
FIG. 9 is a pictorial illustration of how to record data on the memory device of an intelligent heater tube.

Referring to FIG. 9, a pictorial example of how to connect to the memory device 125 of the intelligent heater tube 69 when running a test of a sample fuel is shown. The intelligent heater tube 69 is held in position by lower clamp 107. The ground stick 183 of the EEPROM 181 is contained inside of center bore 179 of the enlarged bottom 175.

To write to and from the EEPROM 181, an IHT writer 127 as shown in connection with FIG. 2A is used. The IHT writer 127 has a data line that connects to a spring-loaded contact 191 that pushes against, and makes electrical contact with, the data plate 185. The other side of the IHT writer 127 connects to ground via lower clamp 107, intelligent heater tube 69 and ground stick 183. The output from the IHT writer 127 can either go directly to the JFTOT®, to a video tube deposit rater, or to a personal computer. Normally, there will be two IHT writers 127. One IHT writer 127 will be located inside of a jet fuel thermal oxidation stability tester (JFTOT®). Another IHT writer 127 will be used to record the deposit information as collected on the test section 177 of the intelligent heater tube 69 as is recorded either (a) manually from a visual inspection or (b) with the Video Tube Deposit Rater. The IHT writer 127 when installed on the test apparatus only communicates with the embedded computer 21 shown in FIG. 2. After the test has been run, the only information lacking on the memory device 125 is recording the heater tube deposit rating. This will be recorded either from a manual inspection of the intelligent heater tube 69 or from a video tube deposit rater, either of which will require a separate IHT writer module 127.

Figure 10:
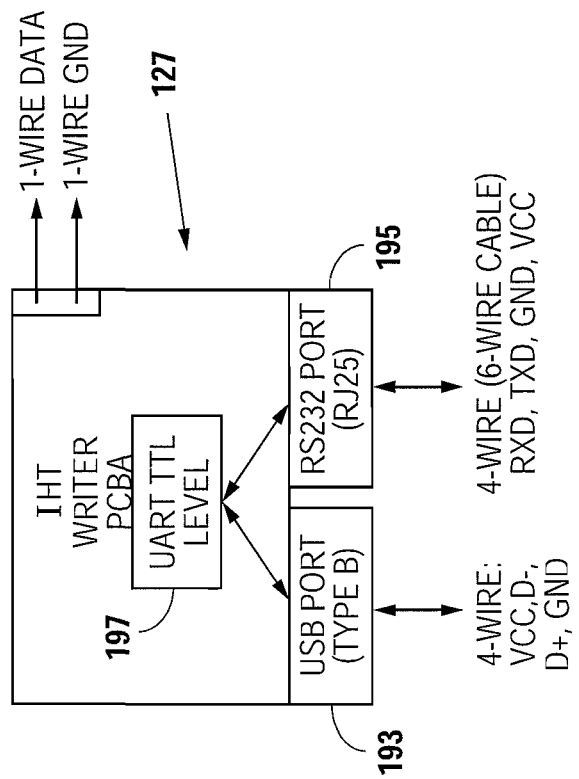
FIG. 10 is a schematic diagram of the writer module used to write on a 1-Wire EEPROM.

Referring now to FIG. 10, the IHT writer module 127 is shown in more detail. The IHT writer module 127 uses 5 Volts DC as its normal power. A USB port 193 is used to connect the IHT writer 127. USB port 193 has four wires for a positive supply voltage VCC, a negative signal voltage D−, a positive signal voltage D+ and a ground GND. Also, the IHT writer 127 has a RS 232 port with four wires being used to transmit data TXD, received data RXD, ground GND, and positive supply voltage VCC. From the IHT writer 127, one wire is for data and one wire is for ground which are used when connecting to the memory device 125 containing the EEPROM 181. The USB port 193 and the RS 232 port 195 supplies data through the IHT writer 127 to the memory device 125. Inside of the IHT writer 127 is a UART TTL level 197 that converts the data to the appropriate form to communicate to EEPROM 181. The abbreviation UART stands for "Universal Acrosynchronous Receiver/Transmitter". TTL is an abbreviation for "Transistor-Transistor Logic".

Figure 11:
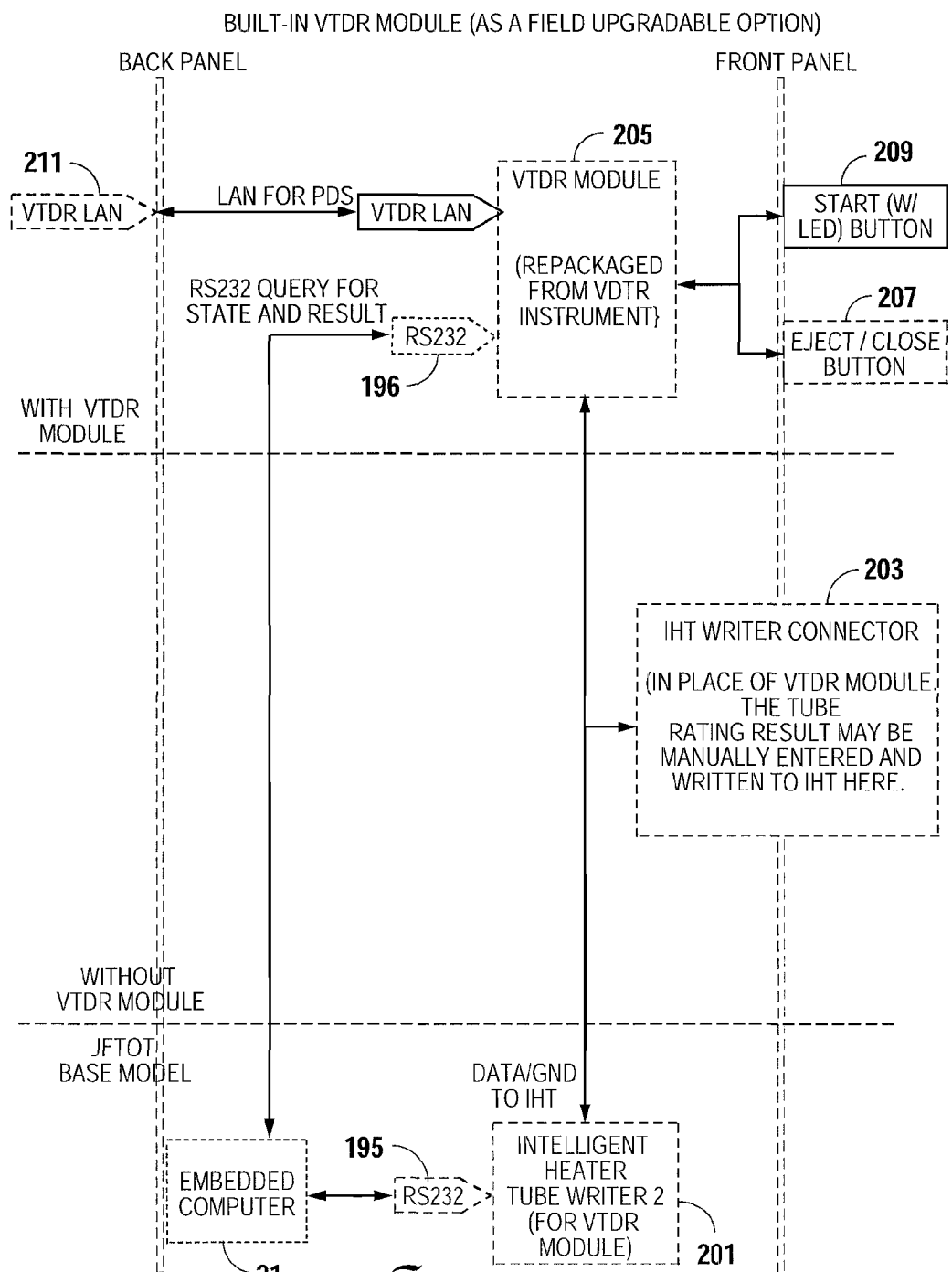
FIG. 11 is a schematic diagram of a built-in Video Tube Deposit Rater for use with an intelligent heater tube.

The JFTOT® 230 Mark III can be configured with or without a Video Tube Deposit Rater, to work with the intelligent heater tube 69 having the memory device 125 as shown in the combination of FIGS. 10 and 11. The embedded computer 21 connects through RS 232 port 195 to the second intelligent heater tube writer 201, which is similar to IHT writer 127. If the test system does not have a video tube deposit rater module, then IHT writer 203 may be used to write to the memory device 125 of the intelligent heater tube 69. In this manner, the IHT writer 203 can be used to manually input the data into the memory device 125.

On the other hand, if the testing apparatus does have a Video Tube Deposit Rater, RS 232 port 196 connects the embedded computer 21 to the Video Tube Deposit Rater (VTDR) module 205. By pressing the eject/close device 207, the door of the VTDR module 205 will open and the intelligent heater tube 69 may be inserted. By pushing the start button 209, deposits collected on the intelligent heater tube 69 during the test are rated. The rating is automatically recorded onto the EEPROM chip 181 (not shown in FIG. 11) contained in the memory device 125.

Also, the image data from the VTDR module 205 may be retrieved by VTDR LAN connection 211.

It is important to remember that two different IHT writer modules are used in the full system. One writer module is used while the heater tube is in the run position. The other writer module is used when the deposit rating is being recorded.

After the information has been recorded on the memory device 125, eject/close device 207 is pressed to open the door to allow removal of the intelligent heater tube 69. Now, all of the information recorded from that test is contained with the intelligent heater tube 69. Since most users keep the recorded data and the heater tube, this allows both to be archived together.

Sample Drive Pump

Figure 12:
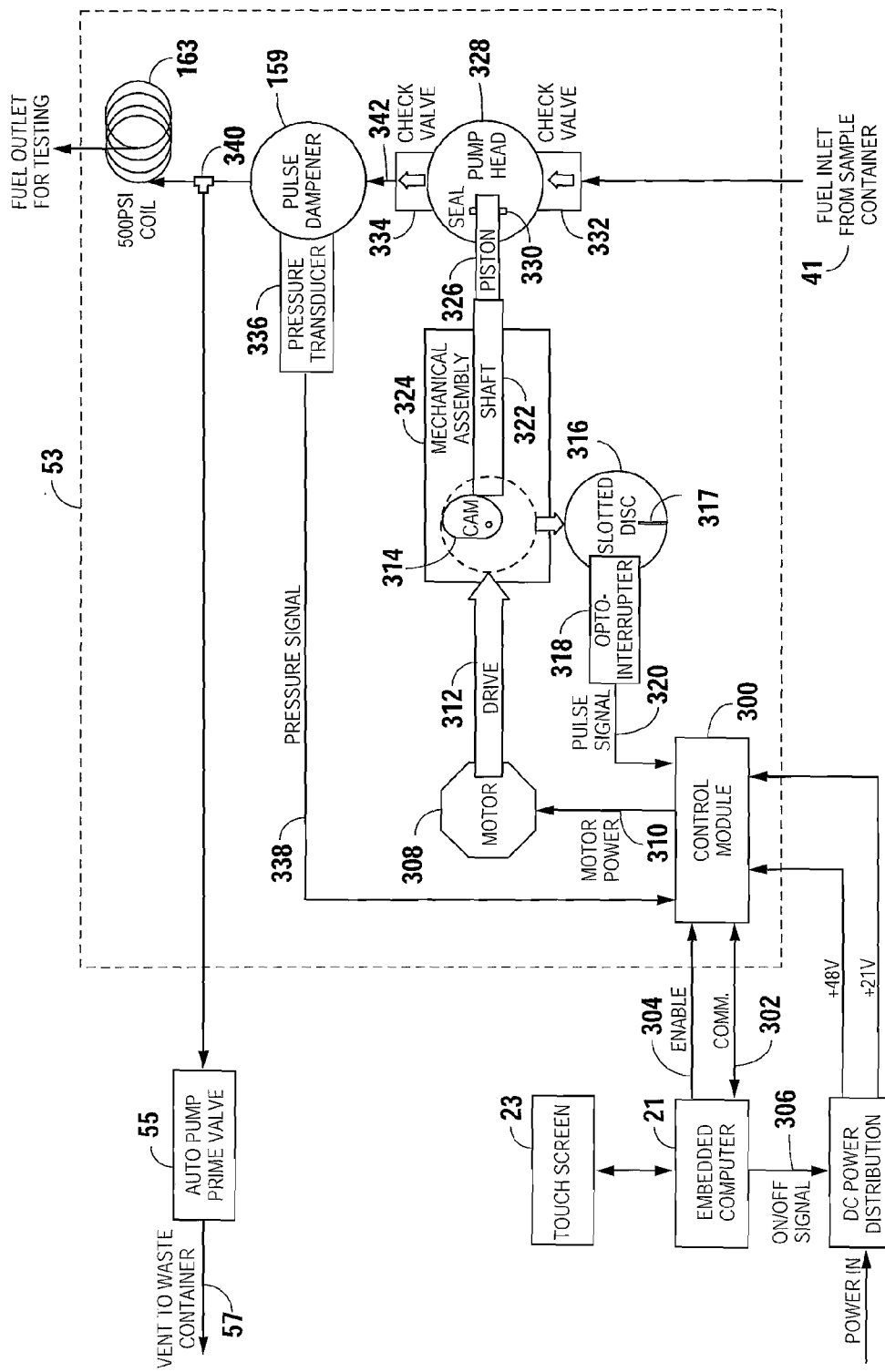
FIG. 12 is a schematic view illustrating use of a low volume, high pressure, single piston pump with sufficient dampening in a thermal oxidation stability tester.

The sample drive pump as shown in FIGS. 2 and 5 is a high-pressure, low-volume pump. Prior versions of the JFTOT that have been available on the market use a dual-piston pump to prevent wide swings in pump outlet sample flow during strokes of the piston. However, one of the drawbacks of using a dual-piston pump occurs after long periods of non-use where remnants of a test sample can dry and leave a sticky residue on the check valve. Sticky check valves can make it difficult to prime the pump because once the check valves for one of the pistons becomes operational it has a tendency to allow sample to flow through the now flowing valves and bypass the other stuck check valves. This will require the need to disassemble the piston and clean the check valves. However, a single-piston pump has only one path for sample flow that has to be primed for use. The sample drive pump 53 of the present invention is a single piston pump, but with numerous ways to prevent fluctuations in output flow between strokes of the single piston. The sample drive pump 53 is operated by a control module 300 as shown in the schematic of FIG. 12. The control module 300 receives its power from DC power distribution 99 shown in FIG. 2A. Also, the control module 300 is connected to the embedded computer 21. The embedded computer 21 is operated by touch screen 23. Control module 300 communicates with the embedded computer 21 through communications line 302. Enable line 304 allows the embedded computer 21 to turn the sample drive pump 53 ON or OFF through control module 300.

Also, the embedded computer 21 has an ON/OFF signal 306 to the DC power distribution 99, which ON/OFF signal 306 will turn power ON or OFF to the sample drive pump 53 via control module 300. Therefore, if the embedded computer 21 determines that any part of the JFTOT is not operating properly, including the program, power thereto can be shut OFF. Turning power OFF to the sample drive pump 53 is a safety mechanism in case something is not operating properly.

From the DC power distribution 99, the +48 Volts being supplied through the control module 300 is used to provide motor power 310 to motor 308. Also, DC power distribution 99 provides +21 Volts to operate the electronics contained in the control module 300.

The motor 308 is a stepper motor that will turn incrementally pursuant to pulses received from the control module 300 in the form of motor power 310. By incrementally providing power to motor 308, the motor 308 will incrementally turn, which incrementally turns drive belt 312. The drive belt 312 has teeth therein that mates with a tooth gear (not shown) so there is no slippage between the drive belt 312 and the tooth gear. A tooth gear is provided on both ends of the drive belt 312 as will be explained in detail subsequently.

As the drive belt 312 turns, eccentric cam 314 also turns. Eccentric cam 314 is an off-centered cam with an eccentric shape that rotates in a circle about center as pictorially illustrated. By use of the eccentric cam 314, shaft 322 is pushed during 270° of rotation of the eccentric cam 314, and retracted during only 90° of rotation of eccentric cam 314. A spring (not shown in FIG. 12) continually urges the shaft 322 against the eccentric cam 314. The eccentric cam 314 and shaft 322 are held together by mechanical assembly 324.

Also, as eccentric cam 314 turns, slotted disc 316 also turns at the same rotational speed or a rotational speed directly proportional thereto. By having a slot 317 in the slotted disc 316, an opto-interrupter 318 can sense when the slot 317 passes adjacent thereto and sends a pulse signal 320 to the control module 300. The pulse signal 320 lets the control module 300 know that the motor 308 is running, eccentric cam 314 turning and at what speeds.

As the shaft 322 contained inside of mechanical assembly 324 moves back and forth (i.e., left and right) while pressing against eccentric cam 314, shaft 322 moves piston 326 back and forth inside of pump head 328. Pump head 328 is receiving fuel from the sample container 41 through check valve 332. As piston 326 retracts from pump head 328, a seal 330 prevents leakage around piston 326. Therefore, since check valve 332 is a gravity-operated ball-and-seat check valve, retraction of the piston 326 from the pump head 328 will draw fluid from the sample container 41, through check valve 332, into the pump head 328. When the piston 326 extends into the pump head 328, pressure is increased in pump head 328 which closes check valve 332 and opens check valve 334. Check valve 334, is also a gravity-operated ball-and-seat check valve. While many different types of check valves can be used, a gravity-operated check valve with a large seat area helps prevent sticking after periods of non-use. During non-use, remnants of a test sample may have remained therein, dried up and left a sticky coating, so using a check valve with a large ball and seat provides a larger area to help any pressure across the valve to unstick the valve.

Pressure inside of the pump head 328 of the sample drive pump 53 is anywhere from 500 to 2,500 psi, depending upon the flow rate. In normal operations over 1,000 psi will be seen in the pump head 328. Any gas or air contained inside of pump head 328 will cause the sample drive pump 53 to not operate properly so it is important to remove any air during priming.

By having the eccentric cam 314, piston 326 extends into the pump head 328 during three-fourths (or 270°), of each rotation of motor 328 and eccentric cam 314. However, the speed of the motor can be increased or decreased by changing the pulses that are being feed thereto from the control module 300. By increasing the frequency of the steps and hence speed of motor 308 during the 90° of rotation when the piston 326 is being retracted, the lag time between pumping cycles is decreased. By increasing the frequency of the pulses to motor 308 when piston 326 is being retracted from the pump head 328, the motor can be made to operate four times faster when retracting piston 326. Therefore, by the combination of the eccentric cam 314 and the speeding up of the motor 308 when retracting piston 326, the pump head 328 can be pumping approximately 94% of the time and only spend 6% of the time retracting. This greatly reduces the time of flow pulsations in test fluid being discharged through outlet check valve 334. However, the flow pulsations sent from pump head 328 is further reduced by pulse dampener 159. Pulse dampener 159 receives the pressurized test sample from pressure conduit 342 connected to outlet check valve 334. The pulse dampener 159 has a diaphragm therein (not shown) which has a semi-compressible fluid on one side thereof and the pressurized test sample on the other side. In the present invention, the semi-compressible fluid is alcohol. Therefore, as each pulsation of pressurized test sample is received from check valve 334, pulse dampener 159 acts to smooth out the sample flow fluctuations or pulses.

To further provide dampening of the flow pulses of the pressurized test sample, a restriction is added downstream of the pulse dampener 159 in the form of a 500 psi coil 163. At a flow rate of 3 ml./min., the 500 psi coil 163 will cause a pressure drop of 500 psi. In the preferred embodiment the coil 163 has a 1/16" outside diameter and is made from stainless steel tubing. The inside diameter is 7/1,000 of an inch. In the coil 163, there are approximately four loops about 4" in diameter. The inlet pressure to coil 163 will be approximately 1,000 psi and the outlet pressure approximately 500 psi with a flow rate of 3 ml./min. there through. The pressurized test sample from coil 163 feeds through check valve 59 (see FIG. 2) into the entire system for testing to determine the thermal stability of the fluid under test. While different configurations of quantities of pulse dampeners, sizes of pressure coils and check valve sizes can be used, the components described in this embodiment provide the same flow pulsations as the dual-piston pump used in the previous versions of the JFTOT.

To make sure there is no blockage and that everything is operating properly, pulse dampener 159 has a pressure transducer 336 that provides a pressure signal 338 back to the control module 300. In that matter, the control module 300 can monitor the outlet pressure by the pulse dampener 159 to make sure the pressure is not too high. If the pressure gets too high, the control module 300 can stop motor 308 and stop the test. The control module 300 can further send a signal to notify the embedded computer 21 that the pump has stopped. The embedded computer 21 then turns OFF the remaining parts of the JFTOT. Feedback through pressure transducer 336 is an additional safety feature to ensure that everything is operating properly.

Figure 13:
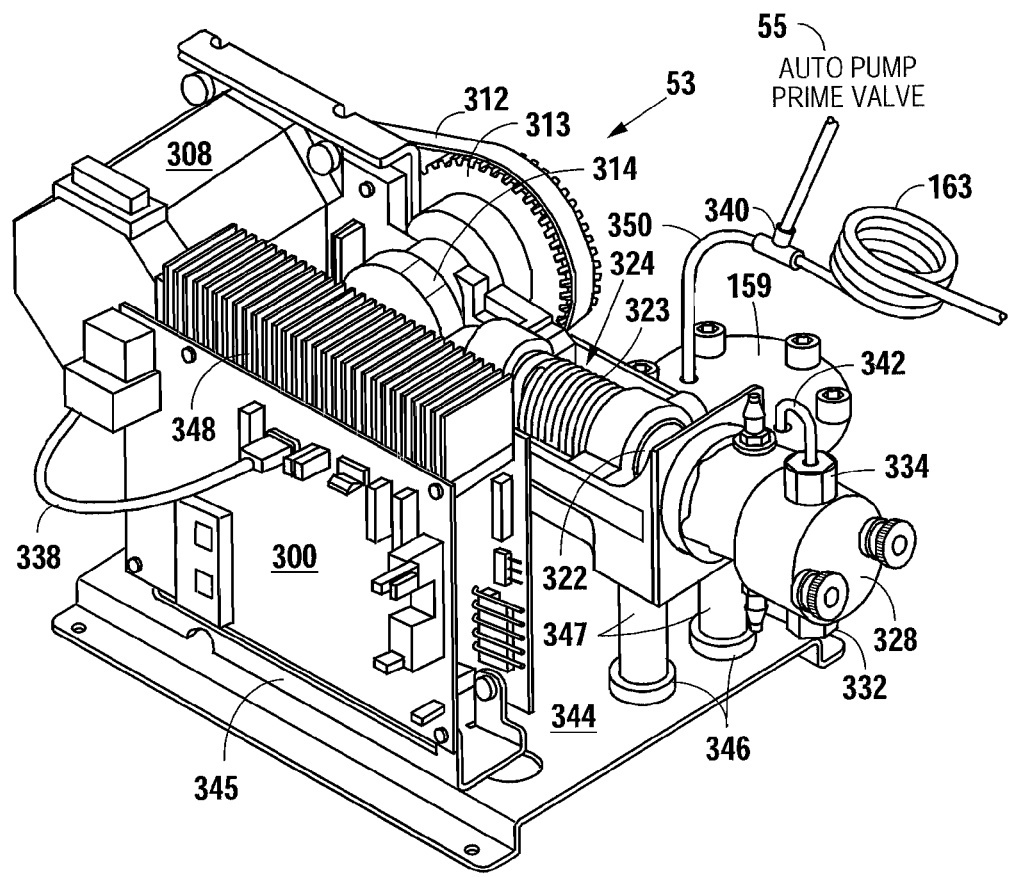
FIG. 13 is a perspective view of the actual pump schematically illustrated in FIG. 12.
Figure 14:
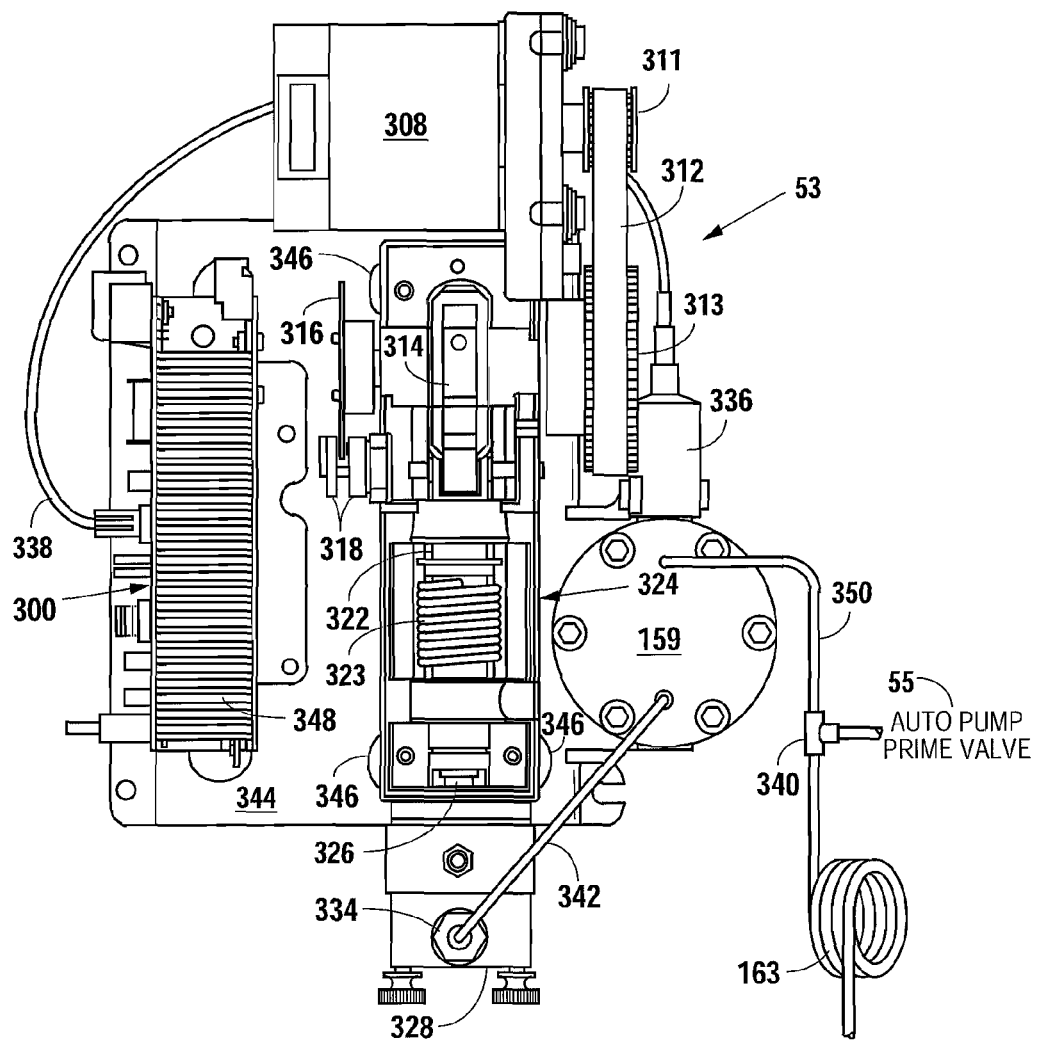
FIG. 14 is a top view of the actual pump schematically illustrated in FIG. 12.

Referring now to FIGS. 13 and 14 in combination, the mechanical layout of the sample drive pump 53 is shown. Everything for the sample drive pump 53 is mounted on base 344. Base 344 has bracket 345 supporting the control module 300 thereon. Heat sink 348 helps dissipate any heat generated by the electronics contained in the control module 300.

Also, the mechanical assembly 324 is attached to base 344 by legs 347 that are secured to the base 344 and rest against vibration dampeners 346. While the leg 347 can be made in many different ways, legs 347 are formed integrally with the mechanical assembly 324.

As the control module 300 turns on the motor 308, belt drive 312 begins to turn. Drive sprocket 311 has teeth therein to match the tooth portion of the belt drive 312. Likewise, cam sprocket 313 has sprockets therein to match the belt drive 312. This ensures the belt drive 312 will not slip on either the drive sprocket 311 or cam sprocket 313.

As the eccentric cam 314 turns, it pushes against shaft 322, which is urged against eccentric cam 314 by spring 323. As the shaft 322 is pushed forward, it pushes piston 326 forward into pump head 328. Likewise, as shaft 322 retracts, piston 326 will retract from pump head 328.

Retraction of the piston 326 from the pump head 328 creates a partial vacuum in pump head 328 causing gravity-operated check valve 332 to open, which draws part of the test sample from sample container 41 into the pump head 328. The withdrawing of the piston 326 from the pump head 328 only occurs approximately 6% of the time. The remaining 94% of the time, the piston 326 is being inserted into the pump head 328 which creates pressure in pump head 328 that closes check valve 332 and opens outlet check valve 334. Pressurized test sample flows through outlet check valve 334 and pressure conduit 342 into pulse dampener 159. After some dampening of the flow fluctuation inside of pulse dampener 159, the pressurized sample flows through flow conduit 350 and T-connection 340 into 500 psi coil 163. The coil 163 provides about a 500 psi pressure drop therein which acts to further dampen the flow fluctuations of the test sample as it comes out of the pulse dampener 159.

Figure 15:
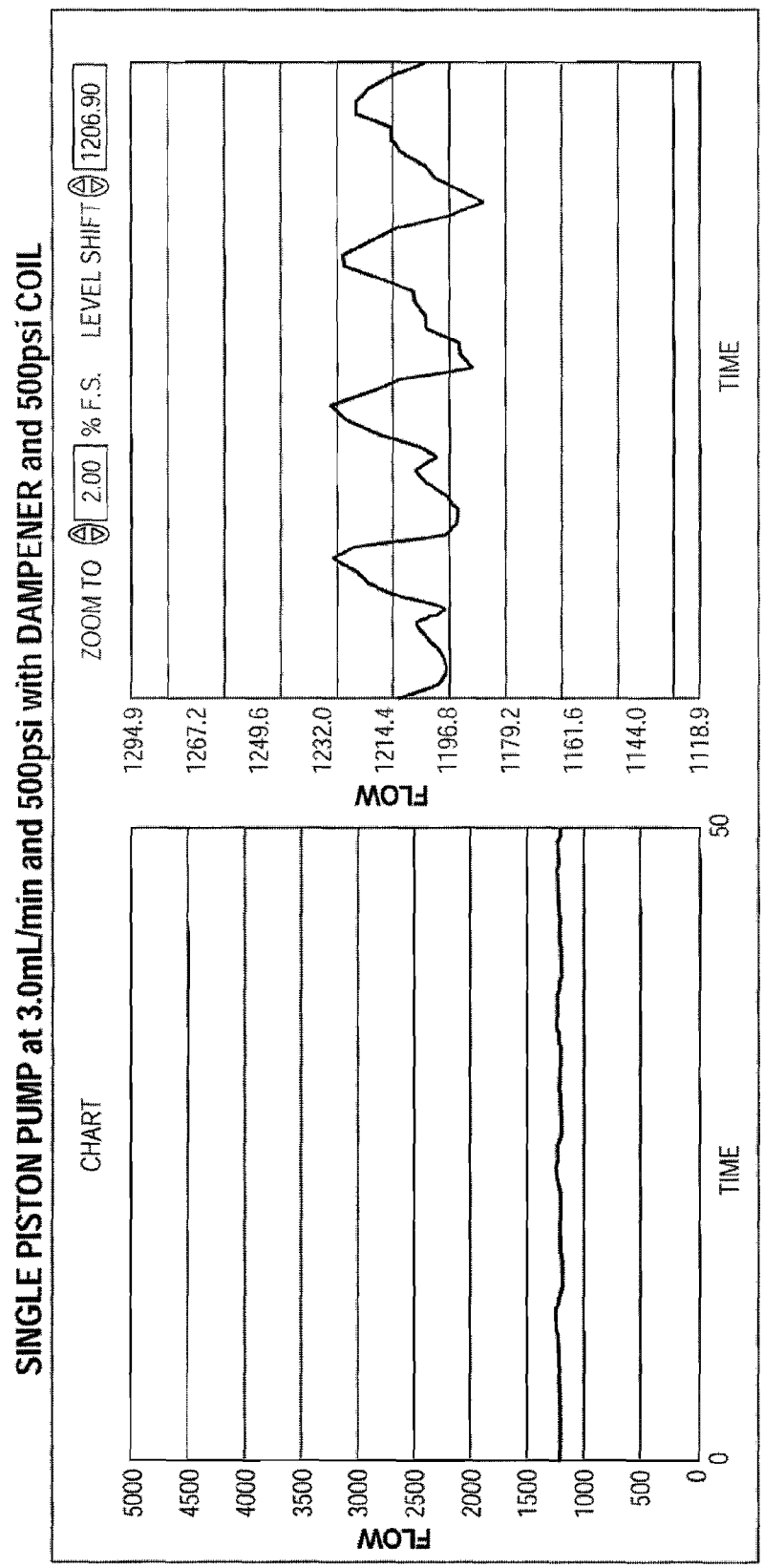
FIGS. 15(a) and 15(b) are graphs showing variations in flow of the fluid under test.

By using the sample drive pump 53 as just described with the single piston head, but with (a) an eccentric cam 314, (b) variable speed stepper motor 308, (c) pulse dampener 159 and (d) a restrictive coil 163, the variations in flow of the test sample have been minimized. Referring to FIG. 15, FIG. 15(a) shows the overall variation in a normal 3.0 mL/min flow versus time. FIG. 15(b) shows an expanded flow variation versus time with the lower part of the chart cut off. The variation in flow of the test sample when compared to the overall flow of the test sample is insignificant. By use of the techniques as just described, a single piston pump can be used as the sample drive pump 53 when testing for thermal stability of fluids, particularly jet fuel.

What we claim is:

1. An apparatus for testing thermal oxidation stability of a test sample such as a hydrocarbon fuel comprising:
   a source of electric power;
   a heater tube connected to said source of electric power for flowing current there through to heat a center section of said heater tube to a predetermined temperature;
   a coolant flow circuit supplying coolant to each end of said heater tube to keep each end thereof near room temperature;
   an aeration circuit with an aeration pump for pumping air to aerate said test simple in a sample container;
   a test sample flow circuit for flowing said test sample around said center section of said heater tube to heat said test sample to said predetermined temperature, said test sample flow circuit including:

a single piston, positive displacement, sample drive pump pumping said test sample from said sample container around said center section of said heater tube;

a differential pressure filter in said test sample flow circuit after said heater tube to filter out any solids that may have formed in said test sample when heated to said predetermined temperature due to oxidation of said test sample;

a differential pressure sensor for measuring differential pressure across said differential pressure filter;

a back pressure regulator for maintaining said test sample being pumped by said sample drive pump at a test pressure high enough to keep said test sample in a liquid phase when heated to said predetermined temperature;

a waste container for collecting such hydrocarbon fuel after said test;

a device for recording said differential pressure and deposits on said center section;

said single piston sample drive pump being driven by a stepper motor with a motor control, output flow from said single piston, positive displacement, sample drive pump having dampening thereon;

said dampening includes a pulse dampener on an output side of a pump head of said single piston, positive displacement, sample drive pump with a restriction downstream of said pulse dampener.

2. The apparatus for testing thermal oxidation stability of said test sample as recited in claim 1 wherein said restriction is a high pressure, low flow rate coil.

3. The apparatus for testing thermal oxidation stability of said test sample as recited in claim 1 wherein said pump head has gravity activated check valves on an inlet and said outlet side.

4. The apparatus for testing thermal oxidation stability of said test sample as recited in claim 1 wherein said single piston sample drive pump has a motor driving an eccentric cam that provides pumping approximately three times longer during each cycle than suction.

5. The apparatus for testing thermal oxidation stability of said test sample as recited in claim 4 where a control module speeds up said motor approximate three times faster during suction than during pumping.

6. A method of testing a test sample in liquid form for thermal oxidation stability comprising the following steps:

aerating said test sample in a sample container with dry air to saturate said test sample with oxygen;

heating a center section of an a heater tube to a predetermined temperature by flowing current there through;

cooling each end of said heater tube by flowing coolant from a coolant flow circuit to said each end;

pumping said test sample at a high pressure, low flow rate, around said center section of said heater tube so that temperature of said test sample is raised to approximately said predetermined temperature;

test filtering with a differential pressure filter said test sample to collect solids formed in said test sample when heated to said predetermined temperature;

maintaining an elevated pressure on said test sample during said pumping step sufficient to keep said test sample from evaporating;

discharging said test sample to a waste container;

recording results from the preceding steps;

dampening said pumping step to reduce variation of flow in said elevated pressure of said test sample during testing; wherein:

(1) said pumping step is with a single piston pump having said high pressure, low flow rate, (2) said dampening occurs on an outlet of said single piston pump, and (3) said dampening is provided by (a) a pulse dampener on said outlet and (b) a restriction on said outlet.

7. The method of testing the test sample in liquid form for thermal oxidation stability as recited in claim 6 wherein said restriction is a high pressure, low flow rate coil.

8. The method of testing the test sample in liquid form for thermal oxidation stability as recited in claim 6 wherein said pumping step includes a variable speed motor that is increased in speed during a suction portion of a cycle, but decreased in speed during a pumping portion of said cycle.

9. The method of testing the test sample in liquid form for thermal oxidation stability as recited in claim 8 wherein said variable speed motor turns an eccentric cam at different speeds that prolongs time of said pumping portion but decreases time of said suction portion of said cycle.

10. The method of testing the test sample in liquid form for thermal oxidation stability as recited in claim 9 wherein said pumping step is with a single piston, positive displacement pump that includes an additional step of a measured flow rate of said test sample.

11. An apparatus for testing thermal oxidation stability of a test sample such as a hydrocarbon fuel comprising:

a source of electric power;

a heater tube connected to said source of electric power for flowing current there through to heat a center section of said heater tube to a predetermined temperature;

a coolant flow circuit supplying coolant to each end of said heater tube to keep each end thereof near room temperature;

an aeration circuit with an aeration pump for pumping air to aerate said test simple in a sample container;

a test sample flow circuit for flowing said test sample around said center section of said heater tube to heat said test sample to said predetermined temperature, said test sample flow circuit including:

a single piston, positive displacement, sample drive pump pumping said test sample from said sample container around said center section of said heater tube;

a differential pressure filter in said test sample flow circuit after said heater tube to filter out any solids that may have formed in said test sample when heated to said predetermined temperature due to oxidation of said test sample;

a differential pressure sensor for measuring differential pressure across said differential pressure filter;

a back pressure regulator for maintaining said test sample being pumped by said sample drive pump at a test pressure high enough to keep said test sample in a liquid phase when heated to said predetermined temperature;

a waste container for collecting such hydrocarbon fuel after said test;

a device for recording said differential pressure and deposits on said center section;

variations in flow output of said single piston sample drive pump are dampened by (a) an eccentric cam to increase pumping time, (b) increasing speed of a pumping motor therein during suction, (c) a pulse dampener on the output thereof, and (d) a high pressure coil also on said output.

12. A method of testing a test sample in liquid form for thermal oxidation stability comprising the following steps:
- aerating said test sample in a sample container with dry air to saturate said test sample with oxygen;
- heating a center section of an a heater tube to a predetermined temperature by flowing current there through;
- cooling each end of said heater tube by flowing coolant from a coolant flow circuit to said each end;
- pumping said test sample at a high pressure, low flow rate, around said center section of said heater tube so that temperature of said test sample is raised to approximately said predetermined temperature;
- test filtering with a differential pressure filter said test sample to collect solids formed in said test sample when heated to said predetermined temperature;
- maintaining an elevated pressure on said test sample during said pumping step sufficient to keep said test sample from evaporating;
- discharging said test sample to a waste container;
- recording results from the preceding steps;
- dampening said pumping step to reduce variation of flow in said elevated pressure of said test sample during testing;
- fluctuations in said elevated pressure are reduced by
  (a) having an eccentric cam turned by a motor in a pump to increase pumping time and decrease suction time,
  (b) varying speed of said motor to increase pumping time and decrease suction time,
  (c) dampening an output from said pump, and
  (d) providing a high pressure restriction downstream of said output.

* * * * *